United States Patent
Simms

(10) Patent No.: US 11,426,137 B1
(45) Date of Patent: Aug. 30, 2022

(54) MEDICAL IMAGING MARKER DEVICE COMPRISING MAIN MARKER PIECE AND SLIDABLE MARKER PIECE, AND METHOD

(71) Applicant: Innovative Ideas LLC, Vacaville, CA (US)

(72) Inventor: Michael Matthew Simms, Vacaville, CA (US)

(73) Assignee: Innovative Ideas LLC, Vacaville, CA (US)

( * ) Notice: Subject to any disclaimer, the term of this patent is extended or adjusted under 35 U.S.C. 154(b) by 67 days.

(21) Appl. No.: 16/791,448

(22) Filed: Feb. 14, 2020

Related U.S. Application Data

(60) Provisional application No. 62/806,810, filed on Feb. 16, 2019.

(51) Int. Cl.
  *A61B 6/00* (2006.01)
  *A61B 90/00* (2016.01)

(52) U.S. Cl.
  CPC .............. *A61B 6/5294* (2013.01); *A61B 6/58* (2013.01); *A61B 6/582* (2013.01); *A61B 6/583* (2013.01); *A61B 6/584* (2013.01); *A61B 90/39* (2016.02); *A61B 2090/3966* (2016.02); *A61B 2090/3983* (2016.02)

(58) Field of Classification Search
  CPC ......... A61B 6/5294; A61B 6/58; A61B 6/582; A61B 6/583; A61B 6/584; A61B 90/39; A61B 2090/3966; A61B 2090/3983
  USPC ................... 378/162–165, 207, 62
  See application file for complete search history.

(56) References Cited

U.S. PATENT DOCUMENTS

| | | | | |
|---|---|---|---|---|
| 4,918,715 A | * | 4/1990 | Krupnick | A61B 90/18 378/162 |
| 5,052,035 A | * | 9/1991 | Krupnick | A61B 6/08 378/162 |
| 5,287,397 A | * | 2/1994 | Dumsha | G03B 42/047 378/165 |
| 5,394,457 A | | 2/1995 | Leibinger et al. | |
| 5,799,059 A | * | 8/1998 | Stembridge | A61B 6/583 378/207 |
| 5,951,475 A | * | 9/1999 | Gueziec | G06T 3/0068 378/207 |
| 5,963,612 A | * | 10/1999 | Navab | A61B 6/4441 378/4 |
| 6,333,970 B1 | * | 12/2001 | LeMaitre | A61B 6/12 378/162 |
| 6,652,142 B2 | * | 11/2003 | Launay | A61B 6/583 378/163 |
| 6,865,253 B2 | * | 3/2005 | Blumhofer | A61B 6/547 378/205 |

(Continued)

*Primary Examiner* — Allen C. Ho
(74) *Attorney, Agent, or Firm* — Olav M. Underdal; IDP Patent Services

(57) ABSTRACT

A medical imaging marker device includes, a main marker body, an outer side visual radiolucent placement indicator, an inner side visual radiolucent placement indicator, an anatomical side visual radiolucent indicator, visual radiolucent length measurement indicator, an attachment system; and a slidable marker piece, including a slidable marker body and a radiopaque marker; such that the slidable marker body is detachably positionable on an image receptor, such that an image of an anatomical target structure taken with the image receptor includes an image portion of the radiopaque marker, which indicates a side orientation of the anatomical target structure.

20 Claims, 8 Drawing Sheets

(56) References Cited

U.S. PATENT DOCUMENTS

| | | | |
|---|---|---|---|
| 6,960,020 B2 * | 11/2005 | Lai | A61B 6/025 378/207 |
| 7,482,601 B2 * | 1/2009 | Lewis | G03F 7/025 378/207 |
| 7,510,325 B2 * | 3/2009 | Endo | A61B 6/583 250/252.1 |
| 7,587,234 B2 | 9/2009 | Owens et al. | |
| 7,643,615 B2 * | 1/2010 | Wang | G03B 42/02 378/165 |
| 7,738,624 B2 * | 6/2010 | Herold | A61B 6/032 378/18 |
| 7,761,138 B2 | 7/2010 | Wang et al. | |
| 7,950,849 B2 * | 5/2011 | Claus | G06T 11/005 378/207 |
| 7,951,345 B2 * | 5/2011 | Lary | G03B 42/04 422/561 |
| 7,978,825 B2 * | 7/2011 | Ngo | G03B 42/047 378/165 |
| 8,014,849 B2 | 9/2011 | Peckham | |
| 8,104,958 B2 * | 1/2012 | Weiser | G06T 7/73 378/207 |
| 8,295,564 B2 | 10/2012 | Hahn | |
| 8,699,670 B2 * | 4/2014 | Graumann | A61B 6/584 378/162 |
| 8,768,026 B2 * | 7/2014 | Ren | A61B 6/544 382/131 |
| 8,777,485 B2 * | 7/2014 | Holt | A61B 6/03 378/207 |
| 8,804,912 B2 * | 8/2014 | Akahori | A61B 6/583 378/163 |
| 8,903,473 B2 * | 12/2014 | Rogers | A61B 90/39 600/431 |
| 9,541,509 B2 * | 1/2017 | Akahori | A61B 6/486 |
| 9,541,822 B2 * | 1/2017 | Folio | G03B 42/047 |
| 10,010,372 B1 * | 7/2018 | Beck | A61B 6/505 |
| 10,869,736 B2 * | 12/2020 | Smith | A61B 90/39 |
| 2016/0100911 A1 | 4/2016 | O'Neill | |
| 2020/0000545 A1 | 1/2020 | Paul | |

\* cited by examiner

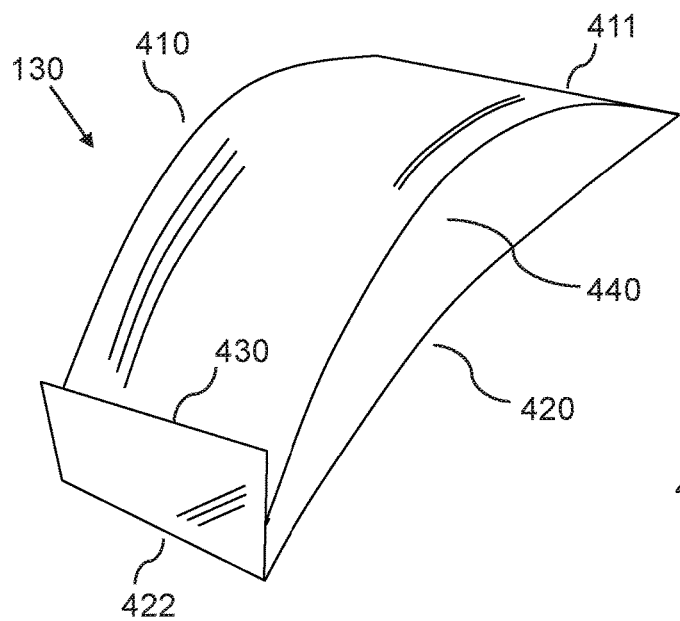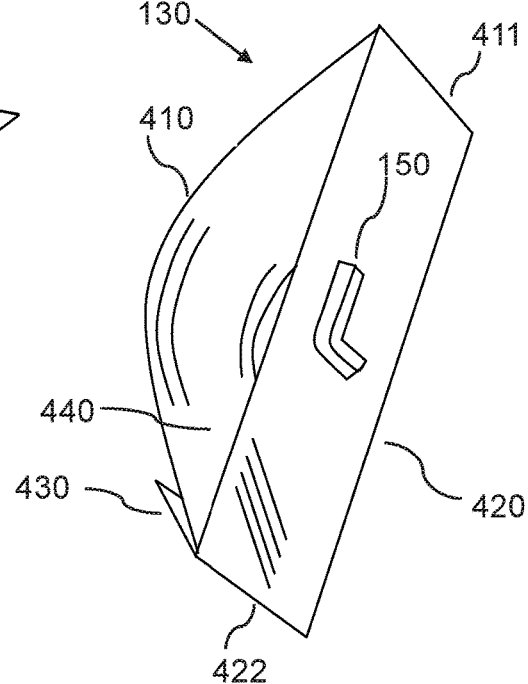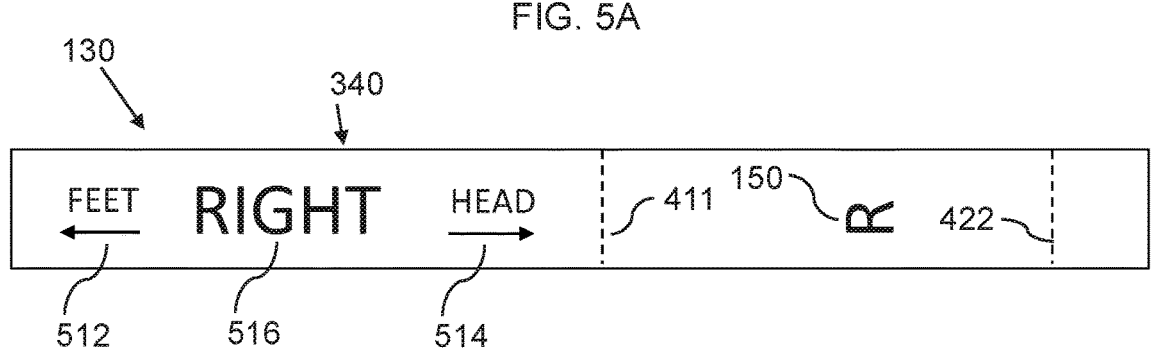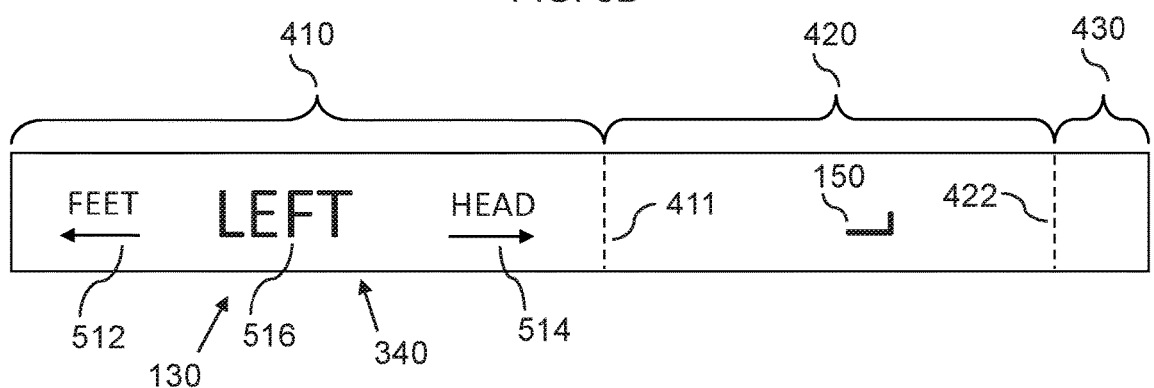

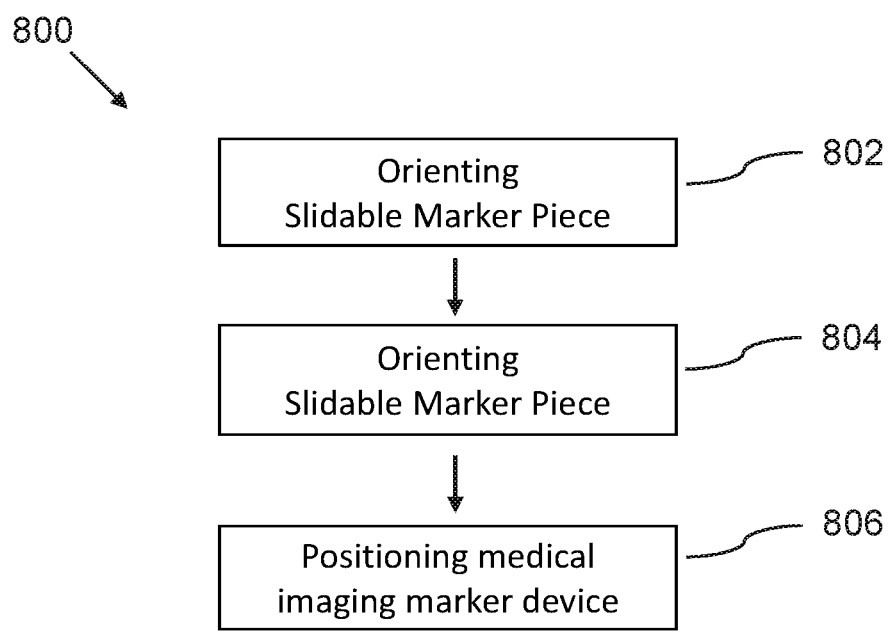

MEDICAL IMAGING MARKER DEVICE COMPRISING MAIN MARKER PIECE AND SLIDABLE MARKER PIECE, AND METHOD

CROSS-REFERENCE TO RELATED APPLICATIONS

This application claims the benefit of U.S. Provisional Application No. 62/806,810, filed Feb. 16, 2019; which is hereby incorporated herein by reference in its entirety.

FIELD OF THE INVENTION

The present invention relates generally to the field of medical imaging, and more particularly to methods and systems for marking medical radiology images, including radiographic and fluoroscopic images.

BACKGROUND OF THE INVENTION

Radiological imaging, including radiography and fluoroscopy, is frequently used during medical procedures. Often, it is difficult to identify the right or left laterality of the anatomy being imaged, without the use of an imaging marker. Current imaging markers cannot be moved once the sterile operating field is established. This is a problem because the patient's anatomy can move or shift during the procedure; causing the imaging marker to superimpose the area of interest.

Currently, radiologic imaging machines have options to add a digital marker to the images post procedure. The problem with that system is that the digital marker is applied post procedure/post exposure, which can lead to human error, and misidentification of the anatomy. Consequently, digital anatomical markers do not meet current "Best Practice" guidelines.

Thus, there is a need in the industry for a reliable and movable imaging marker, used to correctly identify anatomy during radiological imaging, including radiographic and fluoroscopic imaging.

As such, considering the foregoing, it may be appreciated that there continues to be a need for novel and improved devices and methods to correctly identify anatomy during radiological imaging.

SUMMARY OF THE INVENTION

The foregoing needs are met, to a great extent, by the present invention, wherein in aspects of this invention, enhancements are provided to the existing model of anatomical marking device for radiological imaging.

In an aspect, a medical imaging marker device can include:
a) a main marker piece, which can include:
  i. a main marker body, which can be a flat rectangular piece; and
b) a slidable marker piece, including:
  ii. a slidable marker body, which can be slidably connected to the main marker piece, such that the slidable marker slides along an elongated direction of the main marker body; and
  iii. a radiopaque marker, which is connected to the marker body;
wherein the slidable marker body is configured to be detachably positioned on an image receptor;
such that an image of an anatomical target structure taken with the image receptor includes an image portion of the radiopaque marker, which indicates a side orientation of the anatomical target structure.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. In addition, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

FIG. 4A is a top perspective view of a slidable marker of a medical imaging marker device, according to an embodiment of the invention.

FIG. 4B is a bottom perspective view of a slidable marker of a medical imaging marker device, according to an embodiment of the invention.

FIG. 5A is a top view of a slidable marker in a right-side configuration, according to an embodiment of the invention.

FIG. 5B is a top view of a slidable marker in a left-side configuration, according to an embodiment of the invention.

FIG. 8 is a flowchart illustrating steps that may be followed, in accordance with one embodiment of a method or process of preparation of a medical imaging marker device.

DETAILED DESCRIPTION

Before describing the invention in detail, it should be observed that the present invention resides primarily in a novel and non-obvious combination of elements and process steps. So as not to obscure the disclosure with details that will readily be apparent to those skilled in the art, certain conventional elements and steps have been presented with lesser detail, while the drawings and specification describe in greater detail other elements and steps pertinent to understanding the invention.

The following embodiments are not intended to define limits as to the structure or method of the invention, but only to provide exemplary constructions. The embodiments are permissive rather than mandatory and illustrative rather than exhaustive.

Figure 1A:
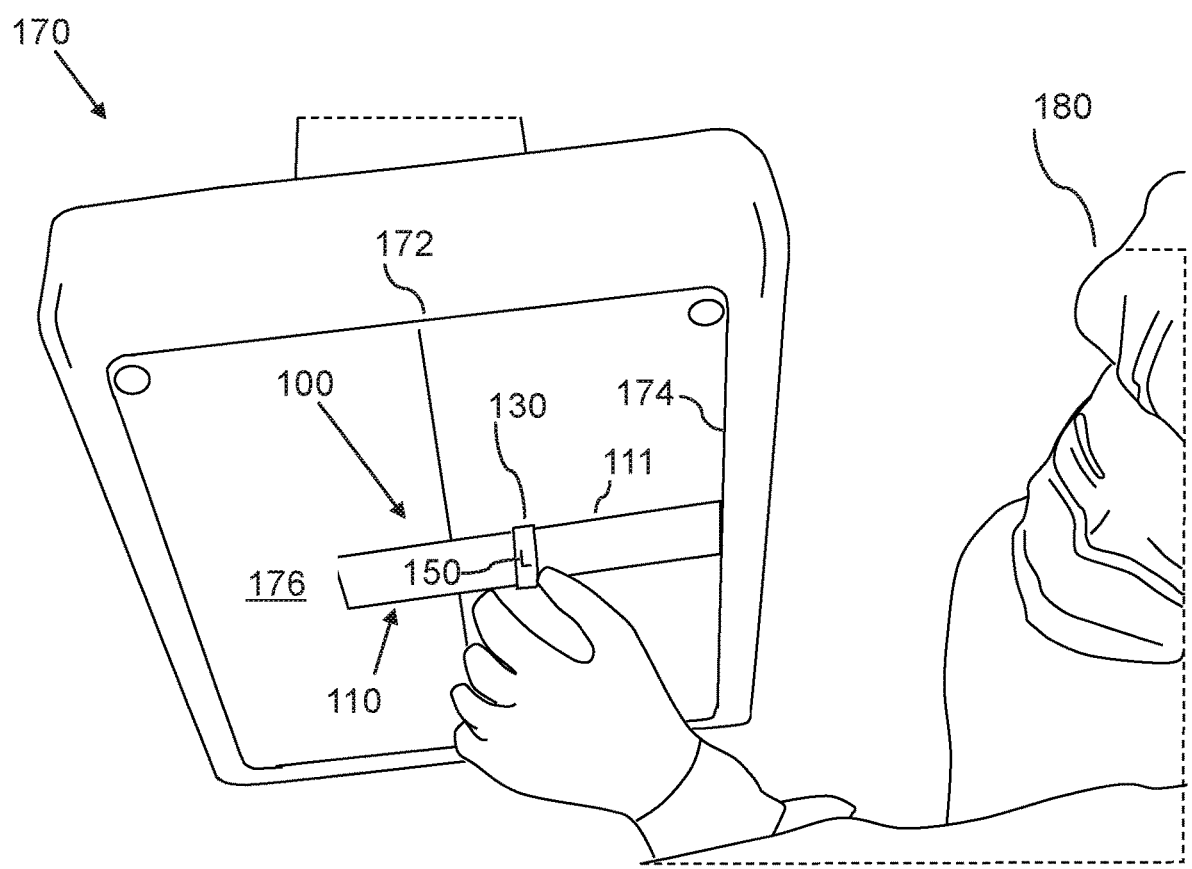
FIG. 1A is a perspective view of a medical imaging marker device mounted on an imaging receptor, according to an embodiment of the invention.

In the following, we describe the structure of an embodiment of a system for medical imaging marker device 100 with reference to FIG. 1A, in such manner that like reference numerals refer to like components throughout; a convention that we shall employ for the remainder of this specification.

In related embodiments, the medical imaging marker device 100 enables medical practitioners to correctly identify anatomy on radiological medical images. As shown in FIG. 1A, the medical imaging marker device 100 allows a user 180 to position an adjustable marker on the image receptor 172 of a radiological machine 170, such as a radiography machine 170 or a fluoroscopy machine 170, and thereby enable correct identification of the patient's anatomy, even if that anatomy were to move during the procedure.

This medical imaging marker device 100 secures to the image receptor 172 of a radiological machine 170. Then, the radiopaque marker is moved into the desired position to correctly identify the anatomy of the patient. The slidable marker can be repositioned due to superimposition of the anatomy or moved into, or out of the field of view as desired.

In an embodiment, as shown in FIGS. 1A, 1B, 2, 3A, 3B, and 3C, a medical imaging marker device 100 can include:

a) a main marker piece 110, which can include:
  i. a main marker body 111, which can be a flat rectangular piece;
  ii. an outer side visual radiolucent placement indicator 312, which can be a text, symbol, or combination of text or symbols, which indicates an outer side 174 of the image receptor 172, when the medical imaging marker device 100 is positioned on the image receptor 172 such that the outer side visual radiolucent placement indicator 312 is aligned with the outer side 174;
  iii. an inner side visual radiolucent placement indicator 314, which can be a text, symbol, or combination of text or symbols, which indicates an inner area 176 of the image receptor 172, when the medical imaging marker device 100 is positioned on the image receptor 172 such that the outer side visual radiolucent placement indicator 312 is aligned with the outer side 174;
  iv. at least one anatomical side visual radiolucent indicator 316, which can be "Left" or "Right", to indicate a left or right side orientation of an anatomical target structure 192;
  v. A visual radiolucent length measurement indicator 318, comprising a plurality of equidistant length indicator bars 319, which can be a plurality of half-inch indicator bars 319, or can indicate centimeters and millimeters; and
  vi. An attachment system 311, which is connected to the main marker body 111, such that the attachment system enables detachable positioning the main marker piece 110 on an image receptor with a bottom of the main marker piece 110 positioned on the image receptor;
    wherein the attachment system 311 for example can be at least one adhesive strip 311 on a bottom side of the main marker piece 110, as shown in FIG. 3B, such that the medical imaging marker device 100 can be removably positioned on the image receptor 172. The adhesive strip can be made from a pressure-sensitive adhesive and can be covered by a cover strip 317 to be removed before use of the imaging marker device 100;

b) a slidable marker piece 130, including:
  i. a slidable marker body 340, which can be slidably connected to the main marker body 111, such that the slidable marker body 340 is configured to slide along an elongated direction 313 of the main marker body 111; and
  ii. a radiopaque marker 150, which is connected to the slidable marker body 340, such as inside the slidable marker body 340 or on a top or bottom surface of the slidable marker body 340, such that the radiopaque marker 150 is configured to indicate a side orientation, which can be left or right;
    wherein the slidable marker body 340 can be configured to be detachably positioned/positionable on an image receptor 172 of a radiological machine 170, which can include an X-ray generator that emits x-rays;
  such that a medical image 190 of an anatomical target structure 162 of a patient 160 taken with the image receptor 172, with the medical imaging marker device 100 positioned on the image receptor 172, includes an image portion 192 of the radiopaque marker 150, which indicates a side orientation of the anatomical target structure 162, which can be a left or right side orientation, to indicate that the medical image 190 shows for example a left or right hand 162, or left or right lung of a patient 160.

In a related embodiment, the main marker piece can further include:

a cover strip 317, which covers the at least one adhesive strip 311, such that the cover strip 317 is removable to expose the at least one adhesive strip 311.

In a related embodiment, the cover strip 317 can extend (i.e. extends) beyond a side of the main marker body 111, such that a tab 319 of the cover strip 317 is exposed to facilitate removal of the cover strip 317.

Figure 6A:
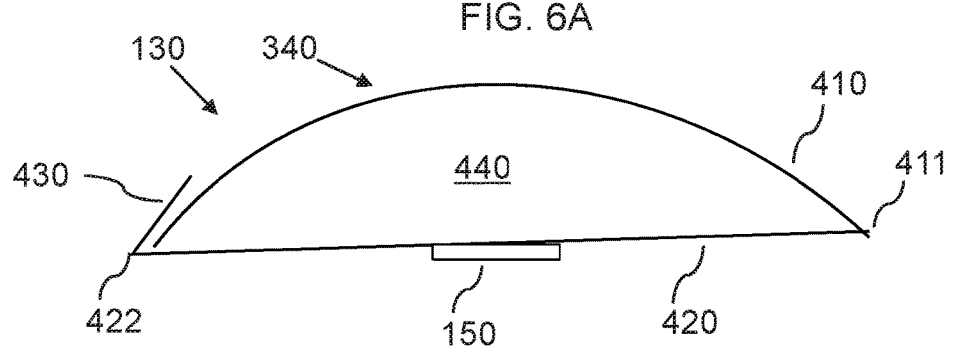
FIG. 6A is a side cross-sectional view of a slidable marker in a folded closed configuration, according to an embodiment of the invention.
Figure 6B:
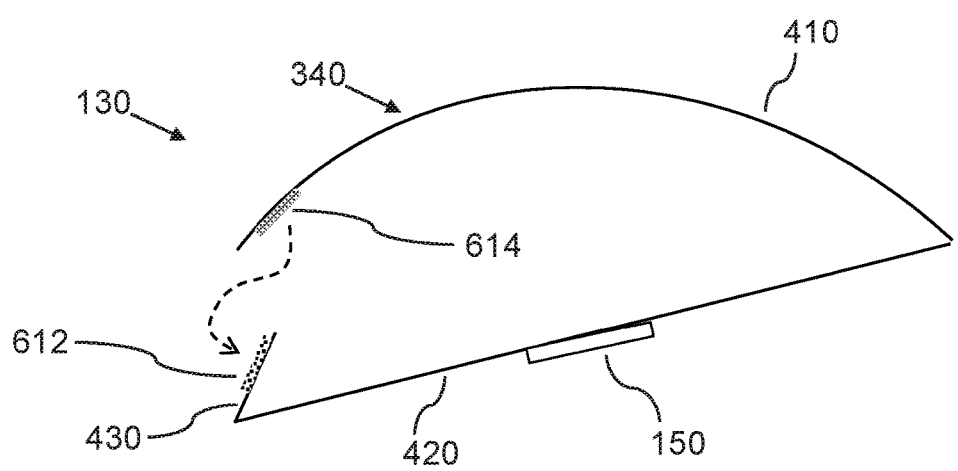
FIG. 6B is a side cross-sectional view of a slidable marker in an open configuration, according to an embodiment of the invention.
Figure 7A:
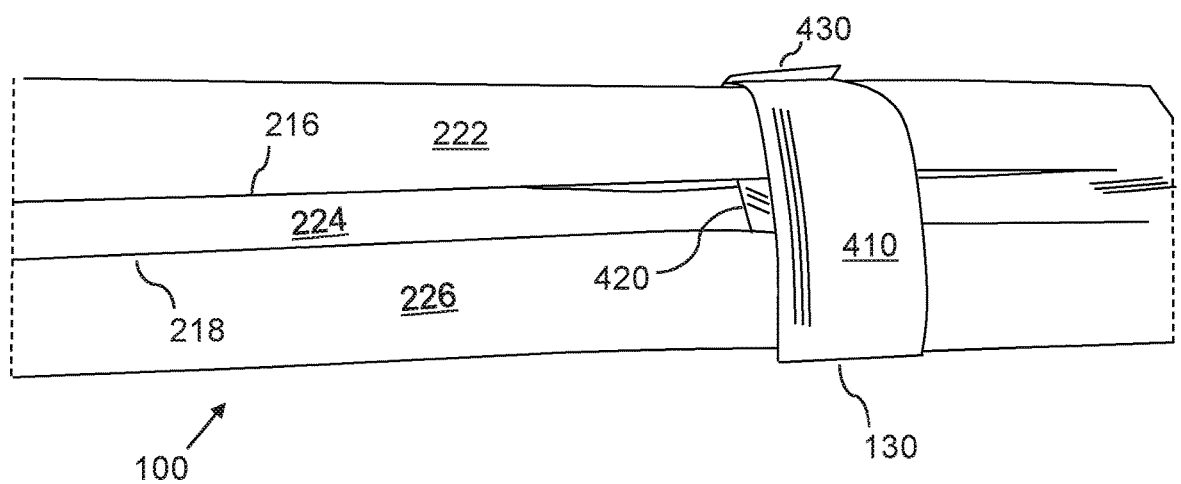
FIG. 7A is a top perspective view of a medical imaging marker device, according to an embodiment of the invention.
Figure 7B:
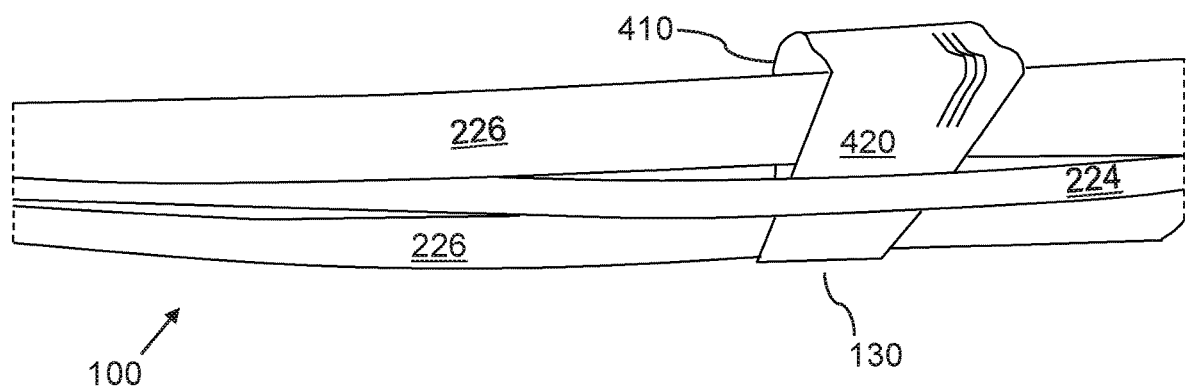
FIG. 7B is a bottom perspective view of a medical imaging marker device, according to an embodiment of the invention.

In a related embodiment, as shown in FIGS. 2, 3A, 4A, 4B, and 5B, the main marker body 111, can further include:

a) A first elongated slit 216, along the elongated direction 313 of the main marker body 111; and b) A second elongated slit 218, along the elongated direction 313 of the main marker body 111, such that the first elongated slit 216 and the second elongated slit 218 are parallel;
    whereby a central portion of the main marker body 111 includes, a top strip 222, a middle strip 224, and a bottom strip 226;
    wherein the slidable marker body 340 is configured as a closed loop with a loop aperture 440, as shown in FIGS. 4A, 4B, and 6A;
    such that the slidable marker body 340 is slidably connected to the main marker body 111 with an inner part 420 of the slidable marker body behind the top strip 222 and the bottom strip 226, and with the inner part 420 of the slidable marker body 340 in a front of the middle strip 224;
    whereby the slidable marker body 340 is configured to be slidable along the first elongated slit 216 and the second elongated slit 218.

In a further related embodiment, as shown in FIGS. 2, 3A, 4A, 4B, and 5B, the slidable marker body 340, can further include:
    a) an outer segment 410;
    b) an inner segment 420; and
    c) a flap segment 430
    wherein a second end of the outer segment 410 is connected along a first fold 411 to a first end of the inner segment 420, and a second end of the inner segment 420 is connected along a second fold 422 to a first end of the flap segment 430;
    such that the outer segment 410 is folded back, such that a first end of the outer segment 410 is adjacent to the second end of the inner segment 420;
    such that the flap segment 430 folds back over an outer end portion of the outer segment 410, such that the first end of the outer segment 410 is held in position by the flap segment 430;
    such that the slidable marker body 340 is configured as a closed loop with a loop aperture 440;
    such that the slidable marker body 340 is slidably connected to the main marker body 111 with the inner segment 420 behind the top strip 222, and the bottom strip 226, and with the inner segment 420 in a front of the middle strip 224;
    whereby the slidable marker body 340 is configured to be slidable along the first elongated slit 216 and the second elongated slit 218.

In a related embodiment, the flap segment 430 can be detachably connected to the outer end portion of the outer segment 410 with a fastener 612, 614, such as a hook and loop fastener 612, 614. Alternatively, the fastener 612, 614 can be a pressure sensitive adhesive, a snap lock, a hook and edge structure, or some other form of fastener.

In a related embodiment, the inner segment 420 of the slidable marker body 340 can be inserted into the main marker body 111 when the slidable marker body 340 is in an open configuration, as shown in FIGS. 5A, 5B, 5C, and 6B, such that the inner segment 420 behind the top strip 222, and the bottom strip 226, and with the inner segment 420 in a front of the middle strip 224.

Figure 1B:
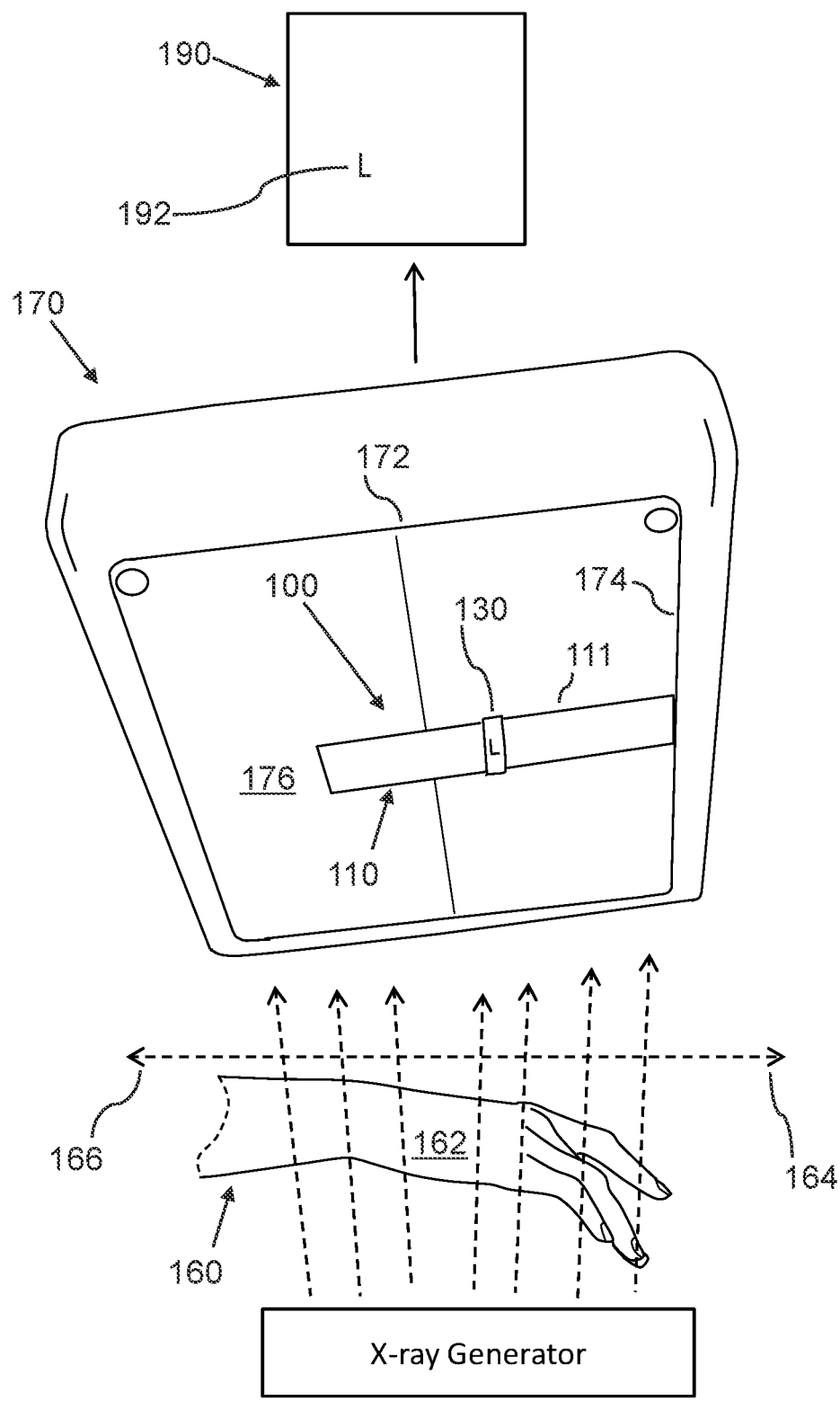
FIG. 1B is a schematic view of a medical imaging marker system, according to an embodiment of the invention.
Figure 2:
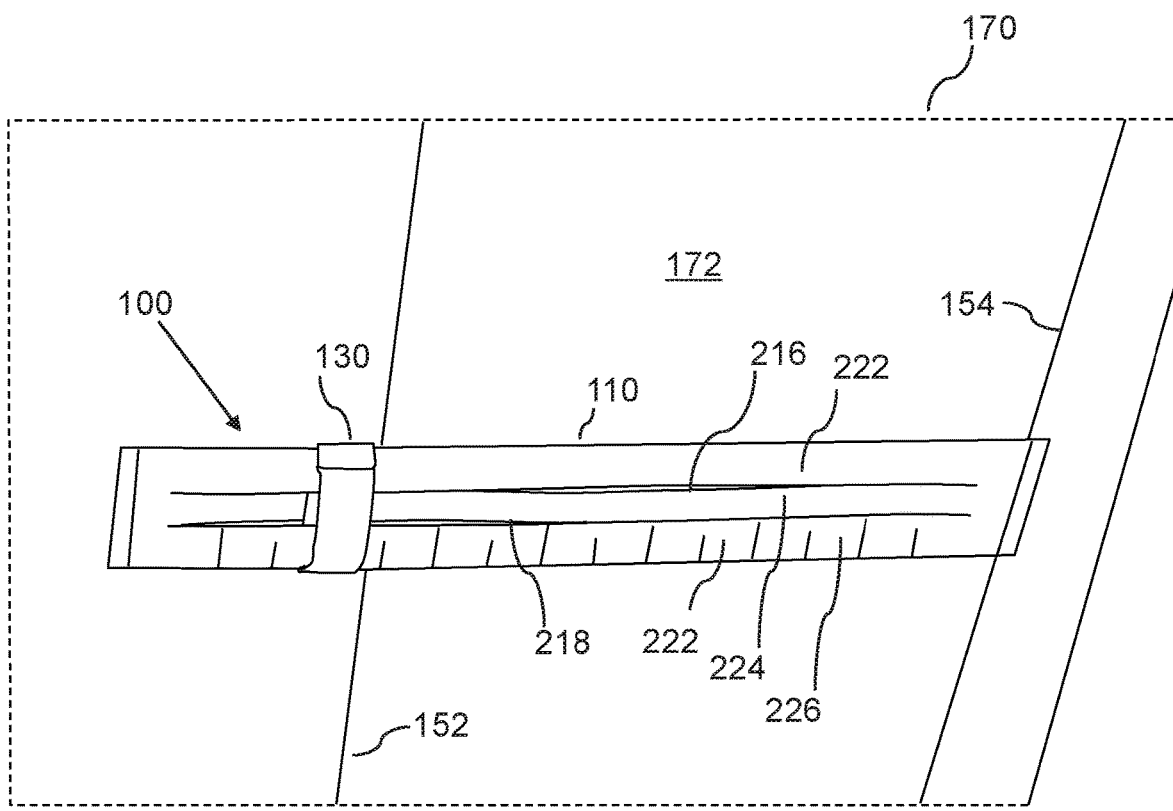
FIG. 2 is a perspective view of a medical imaging marker device mounted on an imaging receptor, according to an embodiment of the invention.
Figure 3A:
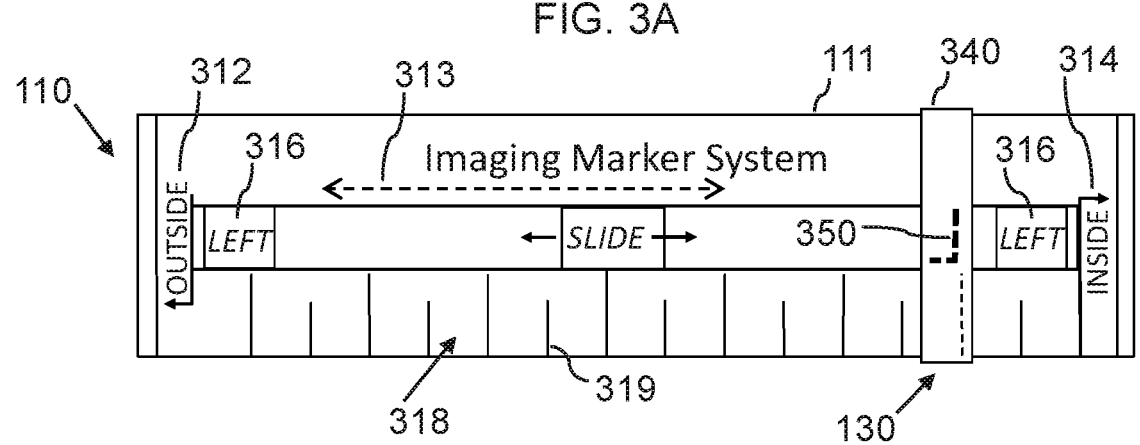
FIG. 3A is a top view of a medical imaging marker device in a left-side configuration, according to an embodiment of the invention.
Figure 3B:
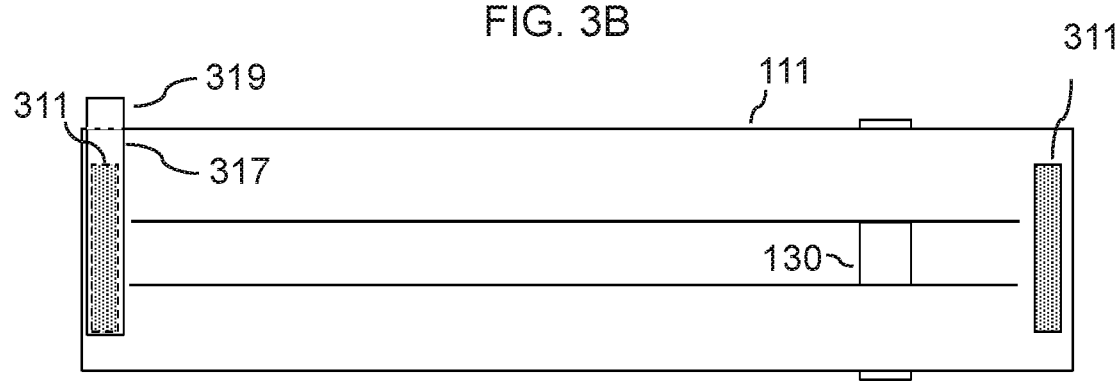
FIG. 3B is a bottom view of a medical imaging marker device, according to an embodiment of the invention.

In a related embodiment, as shown in FIGS. 1, 2, and 3A the medical imaging marker device 100 can be configured as a left-side medical imaging marker device 100, such that the radiopaque marker 150 is configured to indicate a left side, such as by the letter "L", such that a medical image 190 taken with the medical imaging marker device 100 positioned on an image receptor will include an image portion 192 showing an image of the radiopaque marker 150 which indicates that the medical image 190 displays a left side anatomical structure 162 of a patient 160. The medical image 190 can be a digital image 190 or a film image 190.

Figure 3C:
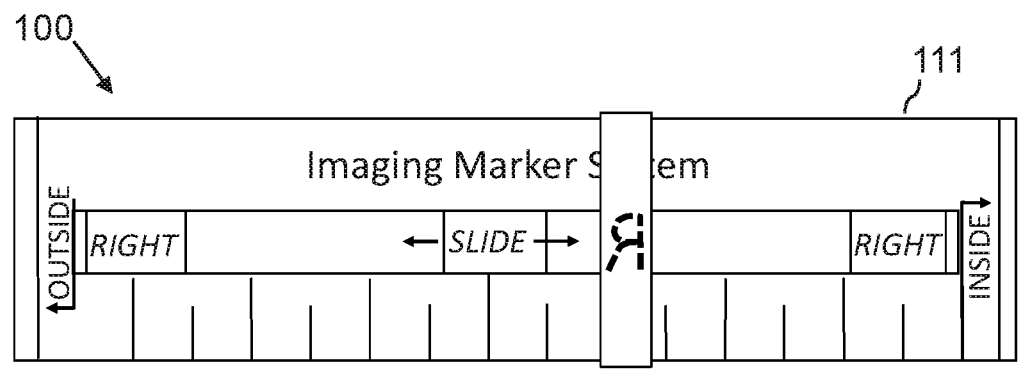
FIG. 3C is a top view of a medical imaging marker device in a right-side configuration, according to an embodiment of the invention.

In a related embodiment, as shown in FIG. 3C the medical imaging marker device 100 can be configured as a right-side medical imaging marker device 100, such that the radiopaque marker 150 is configured to indicate a right side, such as by the letter "R", such that a medical image 190 taken with the medical imaging marker device 100 positioned on an image receptor 172 will include an image portion 192 showing an image of the radiopaque marker 150 which indicates that the medical image 190 displays a right side anatomical structure 162 of a patient 160.

In a related embodiment, the main marker piece 110 and the slidable marker body 340 are made from a radiolucent material, such that the entire medical imaging marker device 100 is radiolucent, except for the radiopaque marker 150. The main marker body 111 and the slidable marker body 340 can be configured with various visual radiolucent indicators 312, 314, 316, 318, 512, 514, which can be seen visually, but do not appear on the medical image. Such visual radiolucent indicators 312, 314, 316, 318, 512, 514 can typically be a printed text, but can also be raised or comprise some additional texture/structure.

In a further related embodiment, as shown in FIGS. 5A, 5B, and 1B, the outer segment 410 of the slidable marker body 340, can further include:
    a) a first anatomical direction indicator 512, which is configured to indicate a first longitudinal direction 164 towards feet of a patient 160, wherein the first anatomical direction indicator 512 can be radiolucent; and
    b) a second anatomical direction indicator 514, which indicates a second longitudinal direction 166 towards a head of a patient 160, wherein the second anatomical direction indicator 514 can be radiolucent for visual indication only; and
    c) An anatomical side visual radiolucent indicator 516, which can be "Left" or "Right" (or "L" or "R"), to indicate a left or right side orientation of an anatomical target structure 192, wherein the anatomical side visual radiolucent indicator 516 can be radiolucent for visual indication only;
    such that the medical imaging marker device 100 can be positioned to indicate a longitudinal orientation 164, 166 of the patient 160, when the medical imaging marker device 100 is positioned on the image receptor 172.

In a further related embodiment, as shown in FIGS. 5A and 5B, the radiopaque marker 150 can be connected to the inner segment 420 of the slidable marker body 340, such that the radiopaque marker 150 is configured to indicate a side orientation, which can be left or right.

In a related embodiment, as shown in FIGS. 5A and 5B, the first and second anatomical direction indicator 512, 514; the anatomical side visual radiolucent indicator 516; and the radiopaque marker 150 can all be positioned on a same/first side of the of the slidable marker body 340; such that the first and second anatomical direction indicator 512, 514, and the anatomical side visual radiolucent indicator 516 will be facing outward and be visible, when the slidable marker body 340 is slidably connected to the main marker piece 110; and such that the radiopaque marker 150 will be facing inward and therefore generally not be visible, when the slidable marker body 340 is slidably connected to the main marker piece 110. Alternatively, the radiopaque marker 150 can be positioned on an opposite/second side of the of the slidable marker body 340, such that the radiopaque marker 150 will be facing outward, but on an inner side of the outer segment 410, such that the radiopaque marker 150 is partially visible, although partially obscured by the outer segment 410.

In a related embodiment, the main marker piece 110 can include additional radiopaque markings, for example to indicate initials of the medical practitioner 180, date of image, etc.

In another related embodiment, the radiopaque marker 150 can be made of lead or lead-equivalent material, or other radiopaque material commonly used for medical imaging, such as X-ray imaging.

In yet another related embodiment, the main marker piece 110 and the slidable marker body 340 can each be made from a radiolucent or semi radiolucent material, such as paper, cardboard, laminated paper, laminated cardboard, coated paper, coated cardboard, plastics, rubber, thin metal, ceramics, wood products, resins, or other radiolucent or semi radiolucent material commonly used for medical imaging.

In various related embodiments, the medical imaging marker device 100 can be configured for one-time use, such that the medical imaging marker device 100 is discarded once removed from the image sensor 172, after a digital imaging session with a patient 160.

In yet another related embodiment, the attachment system 311 can include: hook and loop fastener; double sided adhesive tape, including double sided foam tape; adhesive tape; adhesive, including pressure sensitive adhesive with a cover tape; magnets; clasps; clamps; clips; hooks; snap locks or snap buttons; rubber bands; or other common fasteners, such as common fasteners used in the medical industry.

In a related embodiment, the slidable marker piece 130 can be configured to travel along an elongated direction 313 of the main marker piece 110, such that the slidable marker is stopped at leftmost and rightmost positions.

In a related embodiment, visual markings of the medical imaging marker device 100 can be configured in conventional colors for radiographical imaging, such that red is used for the right anatomical side and blue is used for left anatomical side markers such that a medical practitioner can readily ensure that the correct device is being used.

In another related embodiment, the medical imaging marker device 100 can be configured to be flexible and bendable, such that the medical imaging marker device 100 will fit the small mini-c-arms with very small image receptors, on which the medical imaging marker device 100 can be bent over an edge of the image receptor. The medical imaging marker device 100 device can be configured to fit all sizes of image receptors.

Figure 5C:
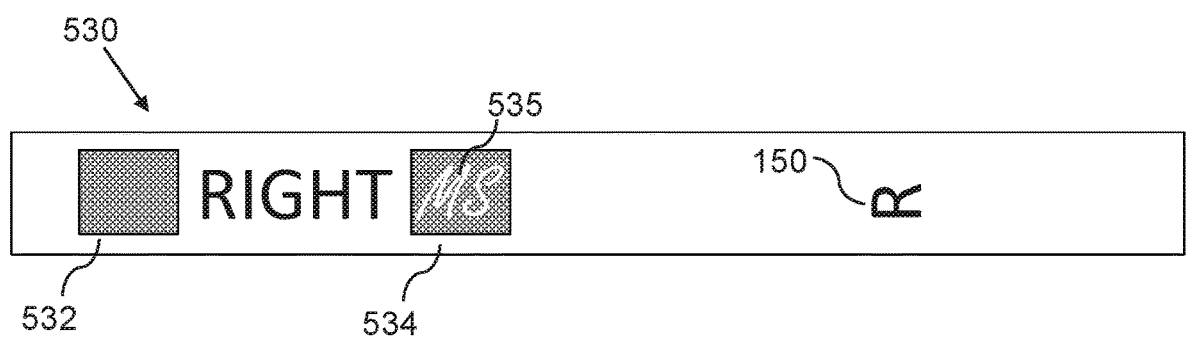
FIG. 5C is a top view of a slidable marker, according to an embodiment of the invention.

In yet another related embodiment, as shown in FIG. 5C, the medical imaging marker device 100 can be configured to include at least one inscription area 532, 534, which can be configured to allow an initial inscription 535, or other text 535 or symbol(s) 535. The inscription area 532, 534 can comprise a thin layer of a scratchable/inscribable material, such as a thermoplastic composition, or a scratchable metal or alloy, and the inscription area 532, 534 can be configured to be semi-radiopaque, such that a faint image representation of the inscription area 532, 534 with the initial inscription 535 will be visible on a medical image 190 taken with the medical imaging marker device 100 positioned on an image receptor 172. The inscription area 532 can be configured as an adhesive tape that is positioned on the medical imaging marker device 100. The inscription area 532 can for example be configured according to well-known principles for inscription area on X-ray markers, such as for example described in U.S. Pat. Nos. 3,063,872A and 6,198,807B1, both of which are hereby incorporated herein by reference in their entirety.

In a further related embodiment, as shown in FIG. 5C, an outer facing surface of the outer segment 410 of the slidable marker body 340 can further include at least one inscription area 532, 534, which comprises a layer of a scratchable and inscribable material, which can be configured to be at least semi-radiopaque (i.e. semi-radiopaque or radio-opaque), such that the at least one inscription area 532, 534, can be configured to receive an initial inscription 535, whereby an image representation of the inscription area 532, 534 with the initial inscription 535 will be visible on a medical image 190 taken with the medical imaging marker device 100.

In an embodiment, as shown in FIG. 8, a method of preparation 800 for preparing the medical imaging marker device 100 for use can include:

a) Orienting 802 the slidable marker piece 130, wherein a medical practitioner orients the medical imaging marker device 100 (in a folded-out configuration as shown in FIGS. 5A and 5B), such that head and feet arrows align with an anatomical position of a patient for exam;

b) Positioning 804 the slidable marker piece 130, by inserting the slide thru the slits of the top and bottom bands (ensuring the head and feet lettering of the slide portion align with the patients anatomical position), and then peeling the flap segment/adhesive tab 430 and securing the slide by creating an arch as shown below. The radiopaque marker 150 will be positioned in the middle of the; and c) Positioning 806 the medical imaging marker device 100, including peeling the adhesive tabs on a back of the medical imaging marker device 100 and placing the medical imaging marker device 100 against the image receptor, such that the medical imaging marker device 100 is aligned with the patients anatomical labeled position.

Here has thus been described a multitude of embodiments of the medical imaging marker device 100, 300 and methods related thereto, which can be employed in numerous modes of usage.

The many features and advantages of the invention are apparent from the detailed specification, and thus, it is intended by the appended claims to cover all such features and advantages of the invention, which fall within the true spirit and scope of the invention.

Many such alternative configurations are readily apparent and should be considered fully included in this specification and the claims appended hereto. Accordingly, since numerous modifications and variations will readily occur to those skilled in the art, the invention is not limited to the exact construction and operation illustrated and described, and thus, all suitable modifications and equivalents may be resorted to, falling within the scope of the invention.

What is claimed is:

1. A medical imaging marker device, comprising:
 a) a main marker piece, comprising:
  a main marker body; and
 b) a slidable marker piece, comprising:
  a slidable marker body, which is slidably connected to the main marker body, such that the slidable marker body is configured to slide along an elongated direction of the main marker body; and a radiopaque marker, which is connected to the slidable marker body, such that the radiopaque marker is configured to indicate a side orientation;

wherein the main marker body and the slidable marker body are made from a radiolucent material; and wherein the main marker body is configured to be detachably positioned on an image receptor;

such that a medical image of an anatomical target structure of a patient taken with the image receptor, with the medical imaging marker device positioned on the image receptor, includes an image portion of the radiopaque marker, which indicates the side orientation of the anatomical target structure.

2. The medical imaging marker device of claim 1, wherein the main marker piece further comprises:
  a) an outer side visual radiolucent placement indicator, which indicates an outer side of the image receptor, when the medical imaging marker device is positioned on the image receptor such that the outer side visual radiolucent placement indicator is aligned with the outer side; and
  b) an inner side visual radiolucent placement indicator, which indicates an inner area of the image receptor.

3. The medical imaging marker device of claim 1, wherein the main marker piece further comprises:
  at least one anatomical side visual radiolucent indicator, which indicates the side orientation of the anatomical target structure.

4. The medical imaging marker device of claim 1, wherein the main marker piece further comprises:
  a visual radiolucent length measurement indicator, comprising a plurality of equidistant length indicator bars.

5. The medical imaging marker device of claim 4, wherein the plurality of equidistant length indicator bars comprise a plurality of half-inch indicator bars.

6. The medical imaging marker device of claim 1, wherein the main marker piece further comprises:
  an attachment system, which is connected to the main marker body, such that the attachment system is configured to enable detachable positioning of the main marker piece on the image receptor with a bottom of the main marker piece positioned on the image receptor.

7. The medical imaging marker device of claim 6, wherein the attachment system comprises at least one adhesive strip on a bottom side of the main marker piece.

8. The medical imaging marker device of claim 7, wherein the main marker piece further comprises:
  a cover strip, which covers the at least one adhesive strip, such that the cover strip is removable to expose the at least one adhesive strip.

9. The medical imaging marker device of claim 8, wherein the cover strip extends beyond a side of the main marker piece, such that a tab of the cover strip is exposed to facilitate removal of the cover strip.

10. The medical imaging marker device of claim 1, wherein the main marker body further comprises:
  a) a first elongated slit, along the elongated direction of the main marker body; and
  b) a second elongated slit, along the elongated direction of the main marker body, such that the first elongated slit and the second elongated slit are parallel;
  whereby a central portion of the main marker body comprises a top strip, a middle strip, and a bottom strip;
  wherein the slidable marker body is configured as a closed loop with a loop aperture;
  such that the slidable marker body is slidably connected to the main marker body with an inner part of the slidable marker body behind a portion of the top strip and the inner part of the slidable marker body behind a portion of the bottom strip, and with the inner part of the slidable marker body in a front of a portion of the middle strip;
  whereby the slidable marker body is configured to be slidable along the first elongated slit and the second elongated slit.

11. The medical imaging marker device of claim 10, wherein the slidable marker body further comprises:
  a) an outer segment comprising a first end and a second end;
  b) an inner segment comprising a first end and a second end; and
  c) a first fold;
  wherein the second end of the outer segment is connected along the first fold to the first end of the inner segment;
  such that the outer segment is folded back, such that the first end of the outer segment is adjacent to the second end of the inner segment;
  such that the slidable marker body is slidably connected to the main marker body with the inner segment behind the portion of the top strip, and the inner segment behind the portion of the bottom strip, and with the inner segment in a front of the portion of the middle strip.

12. The medical imaging marker device of claim 11, wherein the slidable marker body further comprises:
  a flap segment, comprising:
    a first end; and
    a second fold;
  wherein the second end of the inner segment is connected along the second fold to the first end of the flap segment;
  such that the flap segment folds back over an outer end portion of the outer segment, such that the first end of the outer segment is held in a position by the flap segment.

13. The medical imaging marker device of claim 12, wherein the slidable marker body further comprises:
  a fastener;
  such that the flap segment is detachably connected to the outer end portion of the outer segment with the fastener.

14. The medical imaging marker device of claim 13, wherein the fastener comprises a hook and loop fastener.

15. The medical imaging marker device of claim 1, wherein the slidable marker body further comprises:
  a) a first anatomical direction indicator, which indicates a first longitudinal direction towards feet of the patient; and
  b) a second anatomical direction indicator, which indicates a second longitudinal direction towards a head of the patient;
  such that the medical imaging marker device is positionable to indicate a longitudinal orientation of the patient, when the medical imaging marker device is positioned on the image receptor.

16. The medical imaging marker device of claim 1, wherein the slidable marker body further comprises:
  at least one inscription area, which comprises a layer of an inscribable material, which is configured to be at least semi-radiopaque;
  such that the at least one inscription area is configured to receive an initial inscription, whereby an image representation of the at least one inscription area with the initial inscription will be visible on the medical image.

17. A medical imaging marker device, comprising:
a) a main marker piece, comprising:
   at least one anatomical side visual radiolucent, indicator, which indicates a side orientation of an anatomical target structure; and
b) a slidable marker piece, comprising:
   a slidable marker body, which is slidably connected to the main marker piece, such that the slidable marker piece is configured to slide along an elongated direction of the main marker piece; and
   a radiopaque marker, which is connected to the slidable marker body;
wherein the main marker piece is configured to be detachably positioned on an image receptor;
such that an image of an anatomical target structure taken with the image receptor includes an image portion of the radiopaque marker, which indicates a side orientation of the anatomical target structure.

18. The medical imaging marker device of claim 17, wherein the main marker piece further comprises:
a) a first elongated slit, along the elongated direction of the main marker piece; and
b) a second elongated slit, along the elongated direction of the main marker piece, such that the first elongated slit and the second elongated slit are parallel;
whereby a central portion of the main marker piece comprises a top strip, a middle strip, and a bottom strip;
wherein the slidable marker piece is configured as a closed loop with a loop aperture;
such that the slidable marker body is slidably connected to the main marker piece with an inner part of the slidable marker body behind a portion of the top strip and the inner part of the slidable marker body behind a portion of the bottom strip, and with the inner part of the slidable marker body in a front of a portion of the middle strip;
such that the slidable marker body is configured to be slidable along the first elongated slit and the second elongated slit.

19. The medical imaging marker device of claim 18, wherein the slidable marker body filthier comprises:
a) an outer segment comprising a first end and a second end;
b) an inner segment comprising a first end and a second end; and
c) a first fold;
wherein the second end of the outer segment is connected along the first fold to the first end of the inner segment;
such that the outer segment is folded back, such that the first end of the outer segment is adjacent to the second end of the inner segment;
such that the slidable marker body is slidably connected to the main marker piece with the inner segment behind the portion of the top strip, and the inner segment behind the portion of the bottom strip, and with the inner segment in a front of the portion of the middle strip.

20. A medical imaging marker device, comprising:
a) a main marker piece, comprising:
   a visual radiolucent length measurement indicator comprising a plurality of equidistant length indicator bars; and
b) a slidable marker piece, comprising:
   a slidable marker body, which is slidably connected to the main marker piece, such that the slidable marker piece is configured to slide along an elongated direction of the main marker piece; and
   a radiopaque marker, which is connected to the slidable, marker body;
wherein the main marker piece is configured to be detachably positioned on an image receptor;
such that an image of an anatomical target structure taken with the image receptor includes an image portion of the radiopaque marker, which indicates a sine orientation of the anatomical target structure.

* * * * *